(12) United States Patent
Patek et al.

(10) Patent No.: US 6,541,211 B1
(45) Date of Patent: Apr. 1, 2003

(54) APPARATUS AND METHOD FOR SYNTHESIZING COMBINATIONAL LIBRARIES

(75) Inventors: Marcel Patek, Tucson, AZ (US); Safar Pavel, Tucson, AZ (US); Martin Smrcina, Tucson, AZ (US); Eric Wegrzyniak, Tucson, AZ (US); Peter Strop, Tucson, AZ (US); Gary A. Flynn, Tucson, AZ (US); Stephen A. Baum, Tucson, AZ (US)

(73) Assignee: Selectide Corporation, Tuscon, AZ (US)

( * ) Notice: Subject to any disclaimer, the term of this patent is extended or adjusted under 35 U.S.C. 154(b) by 0 days.

(21) Appl. No.: 09/449,222

(22) Filed: Nov. 24, 1999

Related U.S. Application Data

(63) Continuation-in-part of application No. 09/082,038, filed on May 20, 1998.

(51) Int. Cl.[7] .................. C07B 61/00; G01N 21/72; G01N 30/02; G01N 1/00; G01N 33/543
(52) U.S. Cl. .................. 435/7.1; 436/518; 436/155; 436/161; 436/173; 436/174; 436/178; 435/DIG. 43; 435/DIG. 46; 435/DIG. 49
(58) Field of Search .................. 436/518, 155, 436/161, 173, 174, 178; 435/7.1, DIG. 46, DIG. 49, DIG. 43

(56) References Cited

U.S. PATENT DOCUMENTS

| | | |
|---|---|---|
| 5,202,418 A | 4/1993 | Lebl et al. |
| 5,288,514 A | 2/1994 | Ellman |
| 5,324,483 A | 6/1994 | Cody et al. |
| 5,338,831 A | 8/1994 | Lebl et al. |
| 5,342,585 A | 8/1994 | Lebl et al. |
| 5,344,613 A | 9/1994 | Nokihara et al. |
| 5,463,564 A | 10/1995 | Agrafiotis et al. |
| 5,504,190 A | 4/1996 | Houghten et al. |
| 5,510,240 A | 4/1996 | Lam et al. |
| 5,565,173 A | 10/1996 | DeWitt et al. |
| 5,567,391 A | 10/1996 | DeWitt et al. |
| 5,591,646 A | 1/1997 | Hudson et al. |
| 5,593,642 A | 1/1997 | DeWitt et al. |
| 5,609,826 A | 3/1997 | Cargill et al. |
| 5,612,002 A | 3/1997 | Cody et al. |
| 5,650,489 A | 7/1997 | Lam et al. |
| 5,688,696 A | 11/1997 | Lebl et al. |
| 5,702,672 A | 12/1997 | DeWitt et al. |
| 5,723,320 A | 3/1998 | Dehlinger |
| 5,736,412 A | 4/1998 | Zambias et al. |
| 5,741,462 A | 4/1998 | Nova et al. |
| 5,751,629 A | 5/1998 | Nova et al. |
| 5,759,779 A | 6/1998 | Dehlinger |
| 5,763,263 A | 6/1998 | Dehlinger |
| 5,766,556 A | 6/1998 | DeWitt et al. |
| 5,770,455 A | 6/1998 | Cargill et al. |
| 5,846,841 A | 12/1998 | Sepetov et al. |
| 6,083,682 A | 7/2000 | Campbell et al. |
| 6,168,914 B1 | 1/2001 | Campbell et al. |

FOREIGN PATENT DOCUMENTS

| | | |
|---|---|---|
| WO | WO 94/05394 | 3/1994 |
| WO | WO 98/15825 | 4/1998 |
| WO | WO 98/17382 | 4/1998 |
| WO | WO 98/17383 | 4/1998 |
| WO | WO 98/21584 | 5/1998 |
| WO | WO 98/33586 | 8/1998 |
| WO | WO 98/40159 | 9/1998 |
| WO | WO 99/32219 | 7/1999 |
| WO | WO 99/59722 | 11/1999 |

OTHER PUBLICATIONS

Andres et al., 1998, "A novel parallel distributor for dispensing of IRORI™ RF–encoded tags to microkans in 96–well format", Biotech. Bioeng. (Comb. Chem.) 61:93–94.

Bray et al., 1998, "Simultaneous multiple synthesis by the Multpin™ method: techniques for multiple handling, high throughput characterization and reaction optimization on solid phase".

Casebier et al., 1998, "Advances in parallel combinatorial synthesis of mapping Arraystm", 216th ACS National Meeting, Boston (Abst. 024).

Fodor et al., 1991, "Light–directed, spatially addressable parallel chemical synthesis", Macromolecular Chem. 2:401–405.

Frank, 1993, "Spot synthesis: positionally addressable, parallel chemical synthesis on membrane supports", Proc. Eur. Peptide Symp., 22nd, pp. 59–60.

Frank and Guler, 1992, "Spot–synthesis: a novel technique for facile and rapid peptide screening", Proc. Am. Pept. Symp., 12th, pp. 519–520.

Furka, 1988, "More peptides by less labour", Xth Int. Symp. Med. Chem., Hungary (Abst. 288).

Gani et al., 1997, "Permutational organic synthesis in addressable microeactors (POSAM™): an efficient, inexpensive and versatile solid–phase protocol for the preparation of libraries of compounds on the 0.01 to 1.0 millimole (or larger) scale", Tetrahedron Lett. 38:8577–8580.

(List continued on next page.)

Primary Examiner—Padmashri Ponnaluri
Assistant Examiner—Tomas Friend
(74) Attorney, Agent, or Firm—Jiang Lin

(57) ABSTRACT

An apparatus and method for synthesizing a combinatorial library comprising a plurality of chemical compounds such that the chemical composition of each compound is easily tracked. The library compounds are synthesized on solid-phase supports, which are spatially arranged in frames during synthesis according to a predetermined protocol, such that each solid-phase support passes through a series of unique spatial 2D or 3D addresses by which the chemical composition of each compound may be determined at any point during synthesis. Solid-phase supports include hollow tubular-shaped lanterns and gears.

12 Claims, 11 Drawing Sheets

OTHER PUBLICATIONS

Krchnak and Lebl, 1995, "Synthetic library techniques: subjective (biased and generic) thoughts and views", Mol. Diversity 1:193–216.

Lam et al., 1997, "The "one–bead–one–compound" combinatorial library method", Che. Rev. 97:411–448.

Merrifield, "Technical service and development department of the Dow Chemical Co.", 85:2152–2154.

Pavia et al., 1997, "Identifying novel leads using combinatorial libraries: issues and successes", Chimia 51:826–831.

Steele, 1997, "Parallel synthesis methodologides for mixtures and single compounds", $2^{nd}$ Ann. Solid–Phase Synthesis Conference., Cambridge.

Swaze et al., 1998, "Automated parallel synthesis of trisubstituted pyrrolidine and piperidine based combinatorial libraries", $215^{th}$ ACS National Meeting, Dallas, Mar. 29–Apr. 2.

Terret et al., 1997, "Drug discovery by combinatorial chemistry—the development of a novel method for the rapid synthesis of single compounds", Chem. Eur. J. 3:1917–1920.

Xiang et al., 1995, "A combinatorial approach to materials discovery", Science 268:1738–1740.

Baum, filed May 20, 1998, U.S. patent application No. 09/082,038.

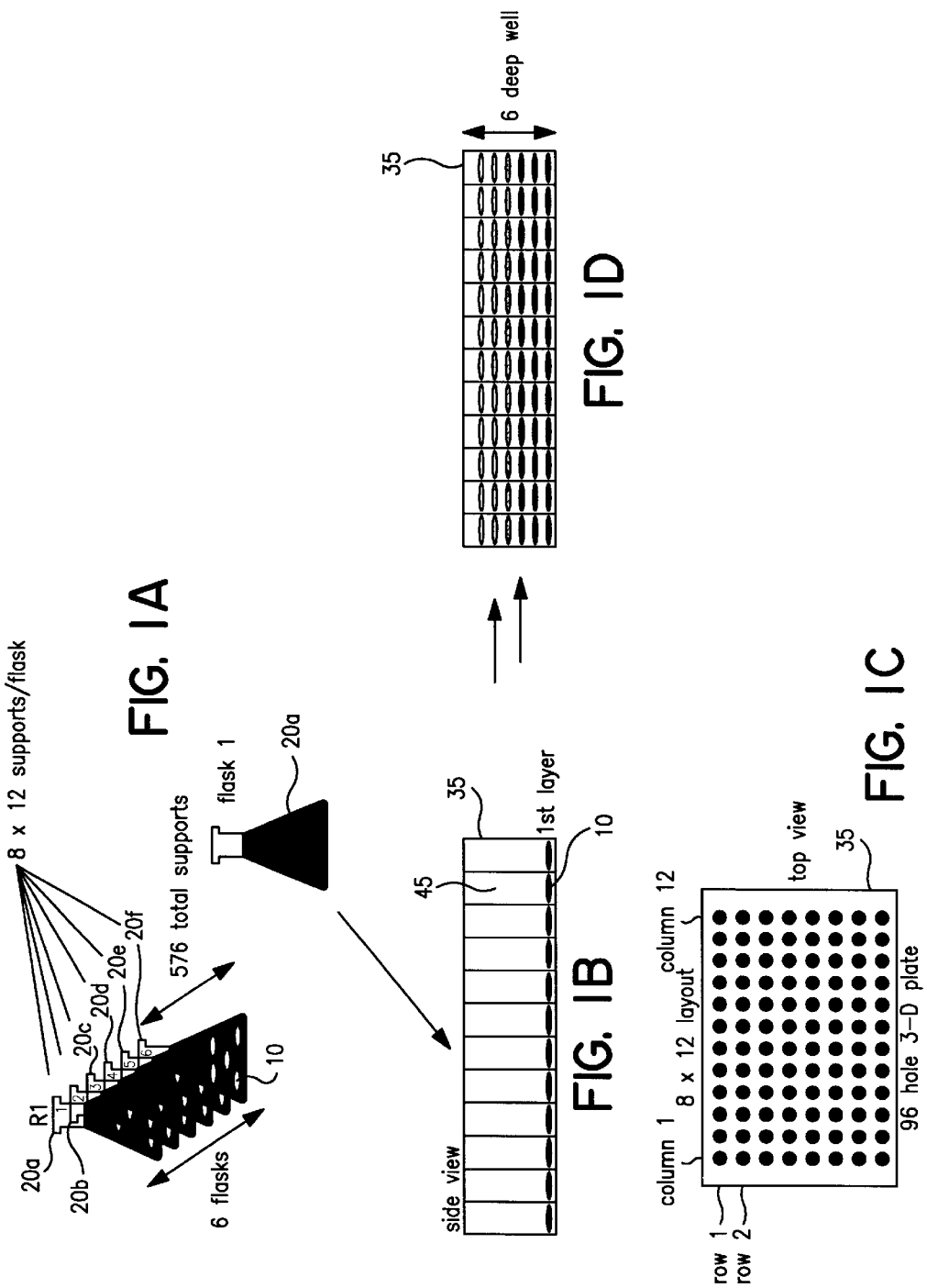

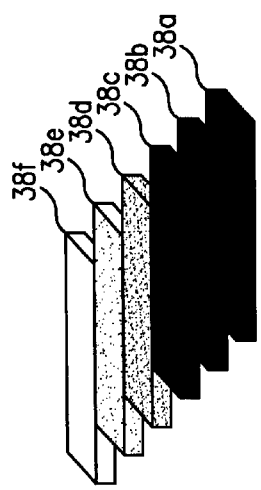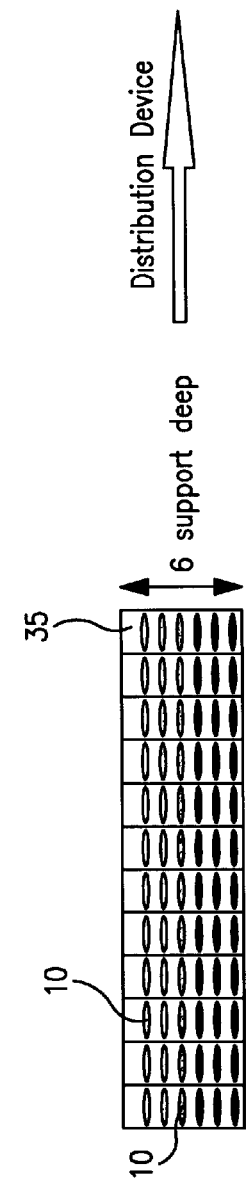
FIG. 4

APPARATUS AND METHOD FOR SYNTHESIZING COMBINATIONAL LIBRARIES

CROSS-REFERENCE TO RELATED APPLICATION

This application is a continuation-in-part of co-pending U.S. patent application Ser. No. 09/082,038, filed May 20, 1998, the entire disclosure of which is incorporated herein by reference.

FIELD OF THE INVENTION

The present invention relates to the field of combinatorial libraries. More specifically, the invention relates to methods of synthesis utilizing arrays of solid-phase supports to produce a combinatorial library of chemical compounds and, additionally, the apparatuses used to carry out those methods.

BACKGROUND OF THE INVENTION

Citation or identification of any reference in section 2 or any section of this application shall not be construed as an admission that such reference is available as prior art to the present invention.

A combinatorial library is a collection of multiple species of chemical compounds comprised of smaller subunits or monomers. Combinatorial libraries come in a variety of sizes, ranging from a few hundred to several thousand species of chemical compounds. There are also a variety of library types, including oligomeric and polymeric libraries comprised of compounds such as peptides, carbohydrates, oligonucleotides, and small organic molecules, etc. Such libraries have a variety of uses, such as identifying and characterizing ligands capable of binding an acceptor molecule or mediating a biological activity of interest.

The library compounds may comprise any type of molecule of any type of subunits or monomers, including polymers wherein the monomers are chemically connected by any sort of chemical bond such as covalent, ionic, coordination, chelation bonding, etc., which those skilled in the art will recognize can be synthesized on a solid-phase support. The term polymer as used herein includes those compounds conventionally called heteropolymers, i.e., arbitrarily large molecules composed of varying monomers, wherein the monomers are linked by means of a repeating chemical bond or structure. The polymers of the invention of this types are composed of subunits or monomers that can include any bi-functional organic or herteronuclear molecule including, but not limited to amino acids, amino hydroxyls, amino isocyanates, diamines, hydroxycarboxylic acids, oxycarbonylcarboxylic acids, aminoaldehydes, nitroamines, thioalkyls, and haloalkyls. In the disclosure of the present invention, the terms "monomer," "subunits" and "building blocks" will be used interchangeably to mean any type of chemical building block of molecule that may be formed upon a solid-phase support.

Various techniques for synthesizing libraries of compounds on solid-phase supports are known in the art. Solid-phase supports are typically polymeric objects with surfaces that are functionalized to bind with subunits or monomers to form the compounds of the library. Synthesis of one library typically involves a large number of solid-phase supports. Solid-phase supports known in the art include, among others, polystyrene resin beads, cotton threads, and membrane sheets of polytetrafluoroethylene ("PTFE").

To make a combinatorial library, solid-phase supports are reacted with a one or more subunits of the compounds and with one or more numbers of reagents in a carefully controlled, predetermined sequence of chemical reactions. In other words, the library subunits are "grown" on the solid-phase supports. The larger the library, the greater the number of reactions required, complicating the task of keeping track of the chemical composition of the multiple species of compounds that make up the library. Thus, it is important to have methods and apparatuses which facilitate the efficient production of large numbers of chemical compounds, yet allow convenient tracking of the compounds over a number of reaction steps necessary to make the compounds.

One method of making combinatorial libraries is described in U.S. Pat. No. 5,510,240 to Lam et al. ("Lam '240 patent"), the disclosure of which is incorporated herein by reference in its entirety. More specifically, the Lam '240 patent discloses a split and mix method of synthesizing combinatorial libraries of bio-oligomers on resin beads, in certain embodiments of which the library contains all possible combinations of monomer subunits of which the bio-oligomers are composed. Although there may be several resin beads containing the same species of bio-oligomer, each resin bead contains only one species of bio-oligomer.

Another example of a method of making combinatorial libraries on divisible solid-phase supports is described in U.S. Pat. No. 5,688,696 to Lebl ("Lebl '696 patent"), the disclosure of which is incorporated herein by reference in its entirety. In the method disclosed in the Lebl '696,each of a set of predetermined species of test compounds is present on a predetermined number of solid-phase supports—preferably on only one—and each solid-phase support has only a single species of test compound.

The use of radio-frequency identification ("RFID") chips to record the steps of library synthesis is also known. See, for example, U.S. Pat. Nos. 5,741,462, 5,770,455, and 5,751,629, as well as WO 98/15826.

A method and apparatus for synthesis of a combinatorial library using a 3-D array of reaction zones is provided in Glaxo's WO 99/32219 ("Glaxo Application"). This application discloses stackable frames having a plurality of holes. Membranes, which act as the solid supports, are trapped between stacked frames, and these membranes are exposed at the frame holes. In an alternative embodiment, solid support beads are placed on flow-through sieves that allow flow-through of reagents around the support beads. Reagents are pumped in from the top and vacated at the bottom or, alternatively, pumped in from the bottom and vacated at the top. The apparatus disclosed allows reagents to be delivered to groups of supports in the X-Z planes or in the Y-Z planes during synthesis steps.

The Glaxo Application also employs a 3-D (X-Y-Z) array of supports. However, instead of using a containment apparatus having true wells in which solid supports are stacked, the Glaxo method employs stackable 2-D (X-Y) frames. The Glaxo Application discloses two distinct embodiments of stackable frame structures. One embodiment sandwiches a membrane between stacked frames, the frames having a plurality of holes. The membranes are solid-phase supports which are held between the frames. The frame holes expose the membranes. The membranes also have holes to allow reagents to pass through the layers of membranes and contact other membranes in the vertical "column" of the array. Another embodiment has sieves in place of the membranes, and free solid supports are placed on each sieve between the frames. The sieves allow reagents to flow vertically from top to the bottom of the stacked 3-D array contacting a vertical column of solid-phase supports resting on sieves.

A major disadvantage with Glaxo's apparatus and method, however, is that after the synthesis is completed, the solid supports, whether as the membrane or the solid-phase support beads suspended on the sieve, are not easily freed from the stacked array while retaining their spatial identities. The frames must be taken apart one by one to gain access to the supports and to provide some means to retain the identities of each support. This requires a burdensome additional step that makes the apparatuses disclosed less attractive for commercial production of libraries.

While methods exist in the art that can be used to produce a library of compounds, there is still a need for methods and apparatuses effective for commercial use to build a large library of compounds quickly and with a minimum of cost. Thus, there is still a need for alternative methods of synthesis that use 2-D or 3-D arrays of solid-phase support as part of the synthesis process for the purpose of commercially making large libraries of compounds efficiently.

Moreover, there is still a need for apparatuses and methods for efficiently synthesizing extremely large libraries, e.g., greater than 100,000 compounds, using 2-D or 3-D arrays as tools in the synthesis.

SUMMARY OF THE INVENTION

The present invention provides methods and apparatuses that use 2-D or 3-D array of solid-phase supports and that may be used to commercially synthesize a library of compounds. In particular a method is provided which may be commercially used to produce large libraries having between about 100,000 to 200,000 compounds. A number of embodiments of methods and apparatuses for synthesizing libraries of compounds are provided herein in accordance with the present invention.

In a first embodiment, in accordance with the present invention, a 3-D array of solid-phase supports is used to provide parallel synthesis. One embodiment of the apparatus which provides this 3-D array is a containment device which has a plurality of wells wherein discrete solid-phase supports can be placed into and stacked in a column. In another embodiment of the apparatus, a 3-D array is formed by stacking a plurality of 2-D frames which have solid-phase supports arranged in an orderly X-Y array. The frames have a plurality of holes arranged in an orderly X-Y array and solid-phase supports can be friction fitted or interlocked into these holes to temporarily hold the supports to the frame during synthesis. Alternatively, the supports can be physically attached to the frames in a manner in which, when desired, they can be easily cut from the frame. Associated with this 3-D array, specific embodiments of the apparatuses are disclosed, in accordance with the present invention, including a 3-D containment plate which has double-drilled holes, a gear-shaped solid-phase supports ("gear") designed to be friction fitted or interlocked into 2-D frame holes, a lantern-shaped solid-phase supports ("lantern"), and ring supports used in conjunction with a containment device having a plurality of wells.

A specific synthesis method is provided, which can be used with an apparatus having a 3-D arrangement of solid-phase supports, in accordance with the present invention. A preferred method provides a monomer or subunit diversity to the library compounds on the solid-phase supports between the X-Y layers in the Z direction. The method comprises: providing reagents to react with solid-phase supports in the X-Z layers, providing reagents to react with solid-phase supports in Y-Z layers, and retrieving columns of solid-phase supports, while retaining their spatial relationships.

A defining characteristic of this first method embodiment using a 3-D array of support is once the array is formed, the supports are generally not moved during the subsequent synthesis steps. Reagents for reacting with the supports are brought to the array and usually a particular reagent is delivered only to a subset of the supports in the 3-D array. Additionally, the size of the library of compound will be limited by the size of the 3-D array.

In a second method embodiment, in accordance with the present invention, the same stackable frames are used as in the first embodiment. Frames having X-Y arrays of solid-phase supports are stacked into 3-D arrays ("stacks"). Instead of a single 3-D array, in this second embodiment a multiple N number of stacks are formed in preparation for making a library of compounds.

In the first synthesis step, each stack numbered 1 to N is completely immersed into separate reactors 1 to N respectively, each reactor having a distinct reagent and a subunit is attached to each support in the stack. After each stack is removed from its reactor, a first randomization occurs by taking one and only one layer (frame) of each original stack, combining these layers to form a new stack. Thus, the first layer or frame from each original stack is grouped to create a first new stack, the second layer or frame from each original stack is grouped to create a second new stack. This reshuffling process is repeated until all the original frames of each old stack are transferred to a set of N number of new stacks. Then, in the second synthesis step, each new stack from 1 to N is immersed in a set of reactors, each reactor having a different reagent.

In the second randomization step, one vertical column of solid-phase supports is removed from each new stack keeping the spatial identification of the supports intact and then reassembled to make a new grouping of 3-D supports. Another vertical column of supports is removed from each new stack and regrouped to another grouping of 3-D supports. This process is repeated until all the supports in the new stack arrays have been regrouped into a N number of new 3-D arrays. In this regrouping, randomization step, only one vertical column of supports is taken from each new stack to make a new grouping of supports. In the third and final synthesis step, the new groupings of supports are each put into separate 1 to N reactors, each reactor having a different reagent.

The apparatuses used with this second embodiment are the same as used in the first embodiment. A preferred embodiment of the frame and solid-phase support is a 2-D frame having a plurality of holes arranged in an X-Y rectangular order. A preferred apparatus comprises gears or lanterns friction fitted or interlocked into the plurality of holes. Additionally, reactors having a capacity large enough for immersion of 3-D stacks are needed.

The defining characteristics of this second embodiment are: (a) many N number of 3-D original stacks are formed; (b) the original stacks do not have solid supports which have a subunit attached in contrast to embodiment one; (c) the solid supports are disturbed from the original 3-D arrays because the supports are moved during the synthesis process when the frames are reshuffled and vertical columns of supports are regrouped; and (d) every solid support in each 3-D stack is completely immersed in the reagent during a synthesis step because the stack is brought to the reagents/reactors. The second embodiment lends itself to large scale production of libraries of compounds because the final number of unique compounds is based on the number N of original stacks made.

The third embodiment, in accordance with the present invention, uses 2-D frames in a "sort and combine" method of synthesis. There is no stacking of the frames into a 3-D array. Instead, the 2-D frames are split during synthesis of the combinatorial library. The method of this third embodiment can be implemented by automation since no rods are required and may be used to generate large libraries, having between about 100,000 to 200,000 compounds.

In this method, a Q number of 2-D frames is chosen. The 2-D frames have rows and columns. Solid supports are placed into reagents for a first synthesis step. Solid supports thus reacted with a single subunit are placed into the frame holes such that the frame has columns of supports which have the same subunit, but between columns, there is a diversity of subunits. This placement provides the first randomization. Each Q number of frames is initially identically prepared. Next, in a second synthesis step, the Q frames are placed into 1 to Q reactors, each having a different reagent. After removal from the reactors, the Q number of frames is split up into subframes to provide the second randomization. M new groups of subframes are regrouped by taking one and only one subframe from each original frame. M represents the number of subframes a frame has been split into. The M new groups of subframes, each are immersed into 1 to M reactors, each reactor having a different reagent. After final synthesis the supports are detached from the subframes and placed into a labeled cleavage plate.

The total number of unique compounds in the library is Q×M×N, where N is the number of columns present in the original 2-D frames, and Q is arbitrarily chosen. The size of the library will be controlled by choice of three variables Q, M and N.

The preferred apparatuses used in this embodiment are 2-D frames. Solid-phase supports such as gears are friction fitted or interlocked into the plurality of holes in the frame. The additional feature of the frame is that it must be easily splittable into subframes. Reactors are need which have capacity for accepting groups of subframes. Additionally, in accordance with a preferred embodiment of the present invention, a 2 row subframe having a RIFD chip is disclosed.

The defining characteristics of this third method embodiment are: (a) user choice of the number of frames Q to use in the synthesis; (b) the solid supports are disturbed from the original 2-D arrays because the supports are moved during the synthesis process when the frames are split and regrouped; and (c) every solid support in each 2-D frame or 2-D subframe is completely immersed in the reagent during a synthesis step because the frame or group of frames is brought to the reagents/reactors. The third embodiment lends itself to large scale production of libraries of compounds because the final number of unique compounds is based on the number Q of original frames used.

All three method embodiments use 2-D or 3-D arrays of supports held in frames to facilitate parallel synthesis on solid-phase supports and to provide spatial identification and thus the synthesis history of the compound produced on a particular support.

There is interchangeability of apparatuses used in the various embodiments described above, in accordance with the present invention. For example, the supports, frames, rods and devices for removing the supports from the frames are interchangeable. A gear design of solid support for use with 2-D frames is provided in accordance with the present invention. A new embodiment of a 3-D containment plate having double-drilled holes and RFID chip is provided in accordance with the present invention.

BRIEF DESCRIPTION OF THE DRAWINGS

Reference is next made to a brief description of the drawings, which are intended to illustrate a number of embodiments of the apparatus and method of making a combinatorial library according to the present invention. The drawings and detailed descriptions which follow are intended to be merely illustrative, and are not intended to limit the scope of the invention as set forth in the appended claims.

FIG. 1a illustrates six flasks 20a–20f, having six different reagents, and 96 solid supports used in the first embodiment of the present invention;

FIG. 1b provides a cutaway side view of a containment well showing the first layer of solid-phase supports after being distributed from the first flask;

FIG. 1c shows a top view of the 96 well plate;

FIG. 1d shows another cutaway side view of the containment apparatus with wells containing all six layers of solid-phase supports, wherein each layer has a different subunit or building block;

FIG. 4 is a mixed side view and perspective view illustrating the final distribution of the solid-phase supports, in which each solid support now provides a unique compound and each layer is distributed into one-layer cleavage plates, 38a–f;

FIG. 14b is a top view of the frame shown in FIG. 14a.

DETAILED DESCRIPTION OF THE INVENTION

Figure 3:
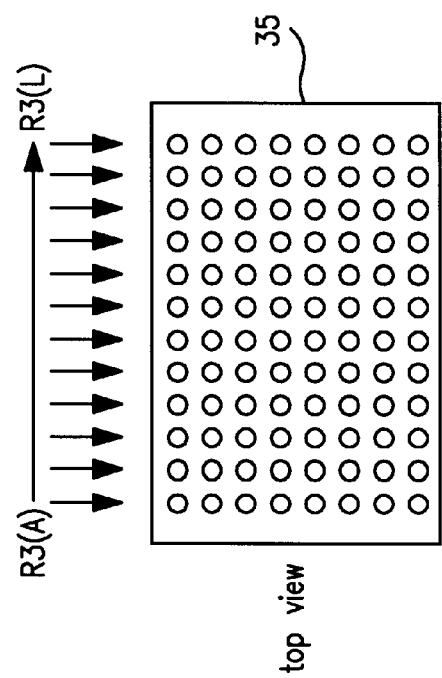
FIG. 3 is a combined diagram and top view of the 96 well containment apparatus, wherein R3(A) through R3(L) represent different reagents delivered into the columns of wells (Y direction of the array) of the apparatus in the third and final synthesis step.

A detailed explanation of the methods and apparatuses in accordance with the present invention with reference to the drawings is provided as follows:

A. Synthesis of Compounds Using Frames Stacked to Provide a 3-D Array

One method of synthesizing solid supports was disclosed in co-pending Baum et. al. U.S. patent application Ser. No. 09/082,038 pending the disclosure of which is incorporated by reference in its entirety. ("Baum Application") (See Baum Application, p. 6, para. 1 and p. 10, para. 2, for discussion of the method utilizing a 3-D array.) The method uses a containment apparatus having a plurality of vertical wells. Free solid-phase supports are "stacked" into each well, each support physically contacting adjacent supports within a well. (See Baum Application, pp. 4–6, in particular, top of p. 5, lines 4–5, discussing a "plurality of discrete supports arranged in a plurality of columns in one or more wells." See also FIGS. 12–17, 23–29 which describe various embodiments of 3-D apparatuses containing a plurality of wells, wherein supports are stacked, and pp. 6–7 which provide Figure captions and discussions of those Figures in pp. 8–41.) The stacking of supports in the containment structure thereby provides an overall 3-D spatial arrangement of supports within the containment apparatus. Thus, after stacking, each support in the 3-D array may be identified by its X-Y-Z position in the array. Once the supports are placed inside the wells, reagents may be directed into sets of wells to react with the supports during steps of the synthesis process. Importantly, because of the open well structure of the containment apparatus, when the synthesis steps are completed, the supports can be easily retrieved from the wells, while retaining the spatial identification of each support.

An example implementing the specific steps of the method is illustrated FIG. 1. The solid support 10 must be of a type which is free and can be stacked vertically in the containment wells. The solid support may be of various types including, but not limited to, those disclosed in co-pending U.S. application Ser. No. 09/082,038 pending, as well as those known in the art. (See Baum Application, FIGS. 12–17, 25–28, which describe various embodiments of solid supports contained in wells wherein "discrete" or free supports are stacked; pp. 6–7 which provide Figure captions and discussion of those Figures in pp. 8–41 and ; p. 21 at para. 1–2 discussing possible shapes of supports.) The solid supports used in the following example is a commercially available Chiron lantern, as shown in FIG. 13.

As shown in FIG. 1a, there are six flasks, 20a–f, each containing a different reagent, R1. As a first synthesis step 96 lanterns 10 are placed into each flask to provide a total of 576 lanterns reacted. The reagents in the flasks attaches to the functionalized surface of the lanterns, thereby forming first synthesis intermediates. It can be seen that six different types of synthesis intermediates are formed by placement in the six flasks, having different reagents.

Next, the 96 lanterns are taken from the first flask 20a and distributed into the 96 vertical wells 45 as the first X-Y layer (Z=1) of supports in the containment apparatus 35, as shown in FIG. 1b. The lanterns from the next flask 20b are then distributed in the same manner forming the second layer of supports within the containment apparatus. This process is repeated until all lanterns from each remaining flask 20c–f are distributed by layers into the containment apparatus.

The containment apparatus 35 must be made of a material which is inert to reagents and can provide proper structural rigidity. A standard 96-well plate, each well approximately 2 ml deep, can be used as 3-D containment apparatus with the proper choice of stackable solid supports. As provided in FIG 1c, which shows a top view of the containment apparatus, the apparatus has 96 total wells placed in an eight by twelve arrangement in the X-Y plane. In the Z vertical direction of the array, the well must have a depth to accommodate the total number of different reagents as shown in FIG. 1d. Because there are six flasks, having six different reagents in the example depicted, the depth of the well must accommodate at least six lanterns. Ultimately, there will be a vertical stack of six lanterns in each well, and each ring will have attached a different subunit, monomer or building block. The configuration or construction of any stackable solid support 10, including the example lanterns, should be designed with the dimensions to prevent relative movement of the supports within the wells 45.

Figure 2:
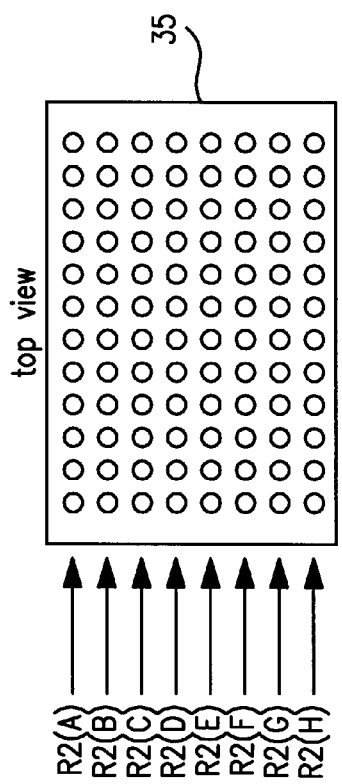
FIG. 2 is a combined diagram and top view of the 96 well containment apparatus, wherein R2(A) through R2(H) represent different reagents delivered into the rows of wells (X direction of the array) of the apparatus in the second synthesis step.

With the supports placed in 3-D array arrangement, the second synthesis step takes place. As shown in FIG. 2, reagent R2(A) is directed to the first row of wells in the X direction of the array, the row consisting of 12 wells. The reagents bond to the particular monomer of each lantern to create second synthesis intermediates. Continuing the process, a different reagent R2(B) through R2(H), as shown in FIG. 3, is directed to successive rows of the containment apparatus. At the conclusion of this step, 48 distinct compounds are formed in the array.

The third synthesis step repeats the previous steps by taking a different set of reagents, R3(A) to R3(L), and directing the reagents successively into row groupings of eight wells pointed in the Y direction of the array. The reagents react with the second synthesis intermediates to create the third and final synthesis product. At the conclusion of this step, there are a total of 576 distinct compounds representing each element of the X-Y-Z combinatorial array.

The last step, as shown in FIG. 4, is the transfer of the solid supports (lanterns) within the containment apparatus 35 into to six separate 96-well plates 38a–f. Each plate will accept only a single X-Y layer of the original 3-D array of supports. Thus, the top X-Y layer of supports is transferred to plate 38a. The next underlying X-Y layer of supports is transferred to plate 39b. The process is repeated until all layers have been transferred. The transfer should be performed in a manner which retains the spatial relationships of the supports. The new plates 38a–f must be properly labeled to identify which X-Y layer is contained, and thus, each transferred lantern may be identified by its original location in the X-Y-Z array of supports.

After the lanterns are transferred to single-layer 96 well plates, the compounds still attached to the lanterns may be stored within these plates. Alternatively, the compounds may be cleaved from the lanterns using a cleavage solution. After cleavage, the compounds may be extracted onto another plate, dried and prepared for biological screening or other purposes for which they may be suited in a manner known in the art.

In sum the synthesis system comprises: (a) a 3-D array of supports; (b) free solid supports; (c) a containment apparatus with a plurality of open wells in X-Y arrangement; and (d) means for removing vertical Z column array of supports from the well from the top or bottom of the 3-D array, once the rounds of synthesis are completed.

The synthesis method comprises: (a) providing free solid supports; (b) providing a containment apparatus having a plurality of open wells; (c) stacking free solid supports into the wells to create a 3-D array of supports; (d) delivering reagents to portions of the 3-D array and; and (e) removing the supports in vertical Z columns.

A particular method of synthesis using the system above comprises: (a) providing an X-Y layer of supports all having one building block attached and diversity of building blocks between X-Y layers in the Z vertical direction of the 3-D array; (b) providing randomization and synthesis by providing reagents first in the X-Z layers and then Y-Z layers of the 3-D array; and (c) removing vertical columns of supports all at once through the well opening, thereby preserving the spatial information of the supports.

In accordance with one embodiment of the present invention, a variation of the above described method of combinatorial synthesis using a single, 3-D array of supports is provided. The formation of the 3-D array of supports is different in this embodiment. In contrast to stacking free solid supports into a separate well containment apparatus, in this variation frames of supports are stacked together to provide a 3-D array of supports. Each 2-D frame defines a single X-Y layer of supports. When stacked, the frames form their own solid support reagent containment compartments, and therefore a separate containment apparatus is not needed.

The supports are either attached temporarily by some mechanical means, such as friction fitting or interlocking into holes of the frames, or the supports come physically attached to the frames but in a manner whereby the supports may be easily cut from the frame.

Figure 5:
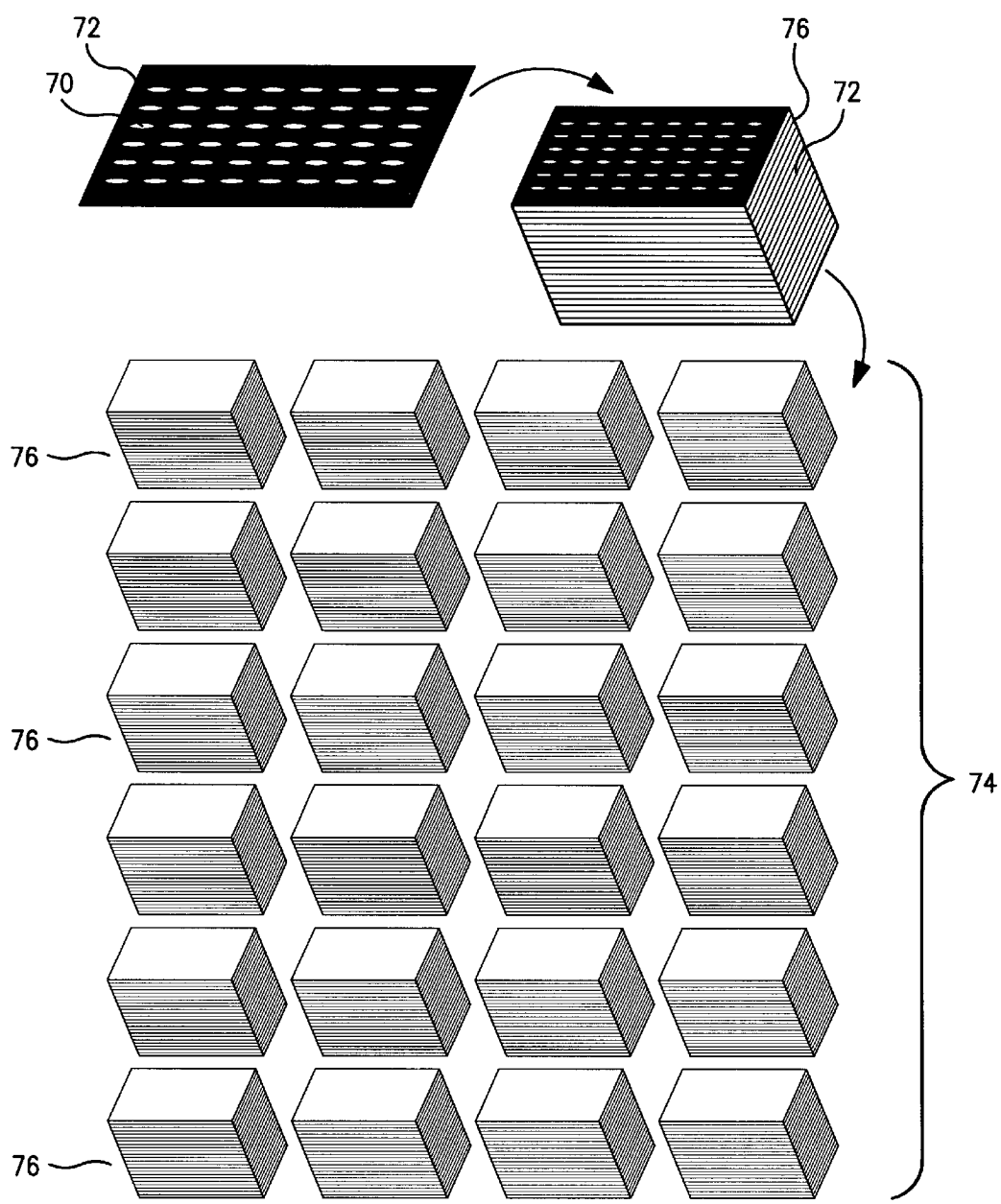
FIG. 5 is a perspective view of a single frame, showing the friction fitted or interlocked gears in a plurality of holes, a stack of frames providing a 3-D array, and a complete set of original "stacks" consisting of 24 total stacks.

Referring to FIG. 5, an example of a single, 3-D stacked frame 76 is shown at frames having gears for solid-phase supports fitted into holes by friction fit or interlocking. Only a single 3-D stack 76 is used in this synthesis embodiment. The method of synthesis is nearly identical to the process used with the open well 3-D containment apparatus. In the first synthesis step, all supports in a single layer or frame are reacted with one type of reagent creating layer diversity. There are several ways to have a frame having all supports attach a single building block. Assuming that free solid supports are used with frames with holes, in which the supports are friction fitted or interlocked, a first way is to have free solid supports such as a lantern or a gear reacted in a reactor such as a flask. The solid supports are then inserted into the holes in a frame and held in place by friction fit or some other means. A second way is to insert the solid supports into the frame first, and immerse the entire frame in a reactor. Assuming that the frame has integral supports attached, immersion of the entire frame into a reactor is the only alternative. Each frame must be immersed in its own reagent. Stacking the layers of frames thereby provides a diversity of monomers or building blocks between layers in the Z direction of the support array.

Figure 7:
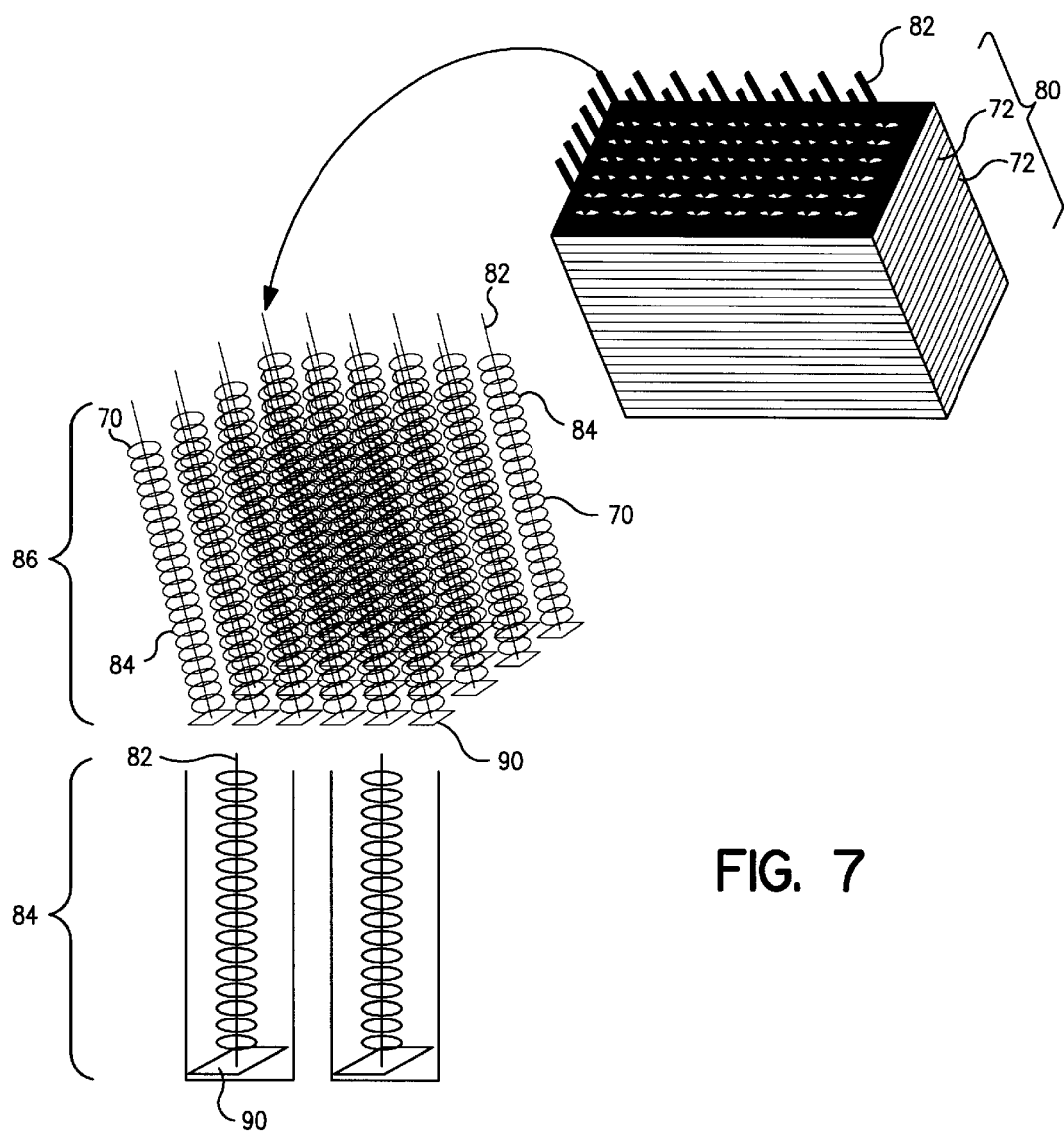
FIG. 7 is a perspective view illustrating the second randomization step of the present method, wherein a single column of supports is taken from each new stack and regrouped to form a new group of supports in a 3-D array and each column is then treated with reagents in a third randomization step.

Once the frames have been stacked, the steps of synthesis and randomization are identical as with the 3-D array using free solid supports and a well containment apparatus. The only difference may be in the last step of removing vertical columns of solid supports from the array. If the solid supports are attached to the frame by friction fit or interlocking, a means must be used to remove individual columns of supports in the Z direction of the 3-D array. If lanterns are used as the solid supports, a rod may be inserted through the holes of the lanterns to capture a single vertical column of rings. As shown in FIG. 7 the rod 82 has a stop-end 90 on one end. The other end of the rod is inserted through the holes of the lanterns and then pulled to free the vertical column of lanterns from the stacked frames. The lanterns thus captured on the rod are spatially intact and may be labeled and stored. Additionally, each ring may be taken out and placed into a single layer cleavage plate and further labeled. If the solid supports are integral to the frame, then there must be an intervening step of cutting the supports from the frame with some cutting device.

Thus, the system comprises: (a) 3-D stackable frames; (b) means for temporarily attaching the supports to the 2-D frame; (c) means for removing the solid supports without disassembly of the 3-D stack, retaining the 3-D spatial relationship of the solid supports; and (d) a channel means to allow reagents in a vertical column in the Z direction to allow supports to contact and react with the reagent directed into the channel.

The method of synthesis is the same as described herein above. The only difference is the addition of an optional cutting step if supports are integral to the frames. A defining feature of this method is that the reagent is brought to the stacked 3-D array. The final compounds formed are identified by their 3-D spatial locations.

B. Split-Mix Synthesis Using Stacked Frames and Rods

In accordance with another embodiment of the present invention, a method is disclosed which uses multiple stacks of frames as shown in FIG. 5. The method involves (a) stacking of frames having a plurality of supports attached to the frames, forming a plurality of identical stacked frames; (b) providing a first synthesis step comprising immersing each stack in a separate reactor to attach a building block to all of the solid supports in the stack of frames; (c) reshuffling the original stacks, for example, such that each first layer of each original stack of frames is grouped in a new stack of frames, each second layer of each original stack of frames is grouped in a new stack of frames, and this process is repeated until all the original stack of frames are reshuffled into new stack of frames; (d) providing a second synthesis step immersing these new stacks each into its own reactor to provide the third step of synthesis; (e) reshuffling the stacks a second time by liberating the columns of supports from each 3-D stack, in a manner that retains the spatial relationship of the supports with the other supports of each column in the Z direction and grouping corresponding columns of supports from the first re-shuffled stacks to form new final stacks; and (f) providing a third synthesis step by immersing each new final stack into its own reactor.

FIG. 5 provides a specific example of the method using particular embodiments of the apparatus. Frames having 48 holes are shown. The solid supports depicted are shaped as gears which may be placed inside the holes by friction fit or interlocking. As shown in the particular example, a complex library having 27,648 compounds is synthesized on solid-phase supports, wherein the compounds are ultimately arranged in a 3-D array, and wherein each compound has a unique 3-D spatial address. In this example, the solid-phase supports comprise gears, which will discussed in more detail below.

As shown in FIG. 5, gear-shaped solid supports 70 ("gears") are placed in plastic gear frames 72. Each frame has a six-by-eight arrangement of holes, which holes have 48 gears inserted. The 24 total frames 72 are stacked together to provide a 3-D stack 76. In this example, 24 identical 3-D set of stacks 74 are created. Given that there are 24 total stacks, 24 frames in each stack, and 48 gears in each frame, the total number of gears in the twenty-four stacks is 27,648. Each stack has 1152 gears.

After the total of 24 tacks are formed, each of these stacks is immersed in its own reactor for the first round of synthesis. Because there are 24 tacks, there are 24 corresponding reactors, each reactor containing a unique subunit, monomer or building block to be attached to the gears. After completion of the first synthesis, each of these 1152 gears in a stack has attached a single building block.

Figure 6:
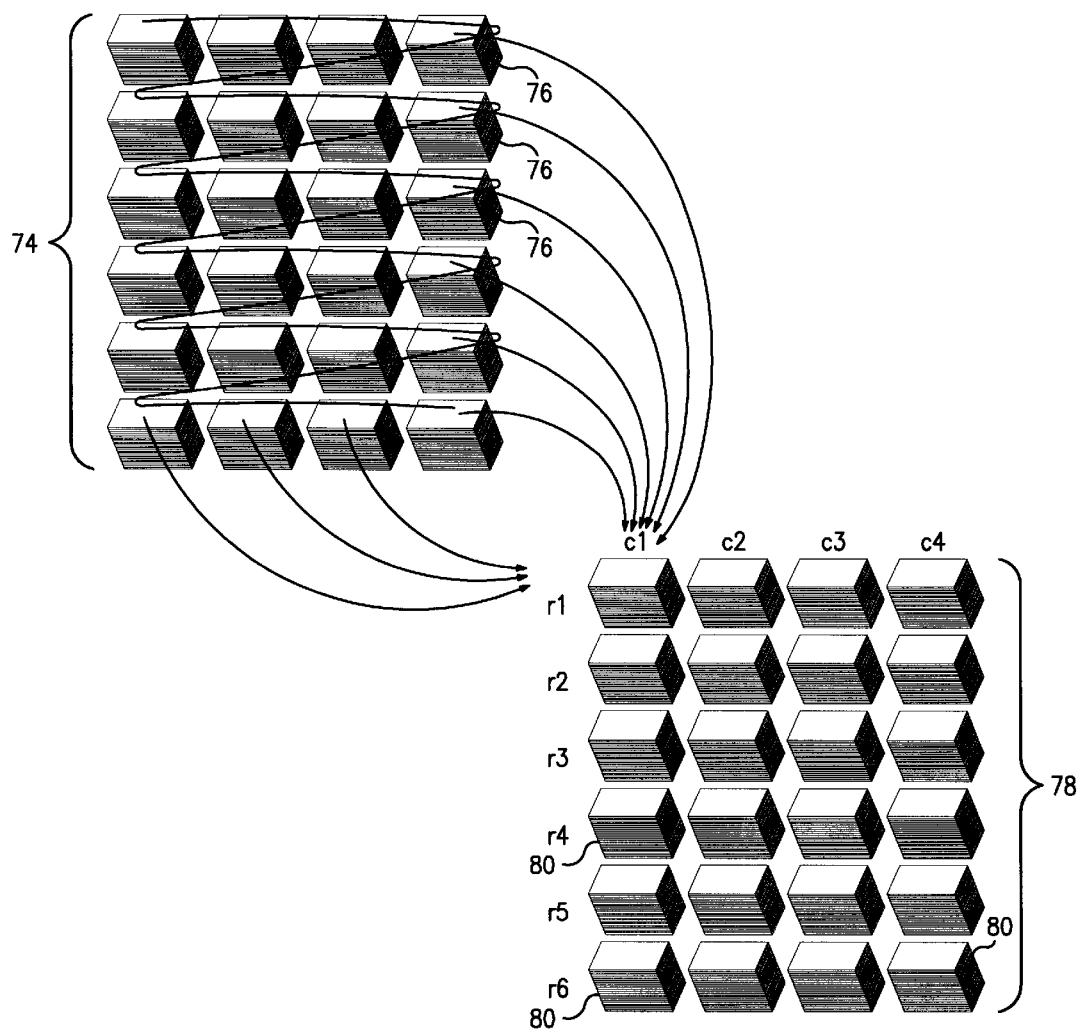
FIG. 6 is a perspective view illustrating the first randomization step involving taking one layer from each original stack to create a new stack and a set of new stacks.

After the first round of synthesis is completed, a first randomization step follows by reshuffling the 24 original stacks into a new stacks. As illustrated in FIG. 6, frames 72 in the first set of 24 original frame stacks 74 are rearranged in a predetermined pattern into a second set of frame stacks 78. In the second set of stacks 78, because all the frames must be accounted for, there are again 24 frame stacks, and each stack consists of 24 frames.

In a particular example of a predetermined pattern, as shown in FIG. 6, the top-most frame of each of the frame stacks in the original frame stack set 74 is arranged in a new frame stack, identified by the label (r1, c1) depicted in newly reshuffled frame stack 78. Similarly, the second layer frames of original frame stacks 74 are arranged in a new frame stack, identified by the label (r1, c2). In this way, all gear frames in original stack 74 are rearranged such that each frame stack in the second set of frame stacks 78 includes one and only one gear frame 72 from each frame stack in the original set of frame stacks 74.

After reshuffling of the frame stacks is completed, each new stack 80, in the set of new stacks 78, is placed in its reactor for the second round of synthesis. Similar to the first round of synthesis, there are 24 reactors, each containing a reagent, with no reagent repeated among the second set of 24 reactors.

As shown in FIG. 7, gears 70 are then liberated from the gear frames 72 and frame stacks 80 and placed on rods 82, thereby forming a column of gears 84. Each of frame stacks 80 yields 48 columns of gears 84 placed on rod 82.

After a second randomization step illustrated in FIG. 7 column of gears 84 are arranged into a group of gear columns 86. Each group of gear columns 86 includes one and only one column of gears from each of the twenty-four set, once-reshuffled frame stacks 80. This re-arrangement results in 24 new groups, each group consisting of 48 gear columns. The liberation of columns of gears may be done manually using rods 82 that have one end having a stop-end 90. The other rod end may be inserted through the holes in each gear.

Each of the group of gear columns 86 are then reacted with a third reagent in a third and final round of synthesis. The method repeats the previous synthesis steps i.e. each group of the newly formed set of twenty-four groups is placed into its own reactor, wherein none of the twenty-four reactors has the same reagent.

After the third round of synthesis has been completed, the gears are stored on their respective rods 82 or removed from their rods and placed in a single layer X-Y plate for future processing, such as cleavage and extraction. One can determine the chemical composition of the compounds on each gear by the 2D spatial address of the gear. Because more than one plate is required to store the entire library of compounds in this example, a label must provide a third component to provide a 3-D spatial identification.

In a preferred embodiment of the apparatuses, Chiron lanterns or gears or other similar supports are placed into holes in frames and held in place by friction fit or interlocking. The means for removing the supports from the frames can be provided in a number of ways depending on whether the supports are attached to the frames by friction fit or whether the supports are physically attached. If the supports are in the frames by friction fit or interlocking, the supports must be taken out from the frames, while preserving the spatial relationship of the supports relative to the other supports. If the supports are physically attached to the frames, the supports must first be cut and then liberated from the frames.

The gears may be pushed or pulled out from the holes of the frames using a variety of tools. One such tool already discussed is a rod 82 having a stop-end 90 as shown in FIG. 7. The support, whether a gear, lantern or another shape, is designed with a hole through the middle. The rod is placed through a vertical line of support holes using one rod end. The stop-end of the rod cannot go through the small hole of the supports and thus a vertical column of supports is caught on the rod and can be liberated from the frames by pulling the tip of the rod. The supports may be conveniently stored on the rods or the supports may be labeled and stored for later cleaving of each unique compound from the supports.

Figure 8:
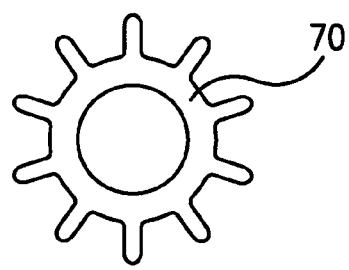
FIG. 8 is a top view of a gear-shaped solid support ("gear") made by Chiron.

If the supports are attached to the frame, the supports must first be cut from the frame before removal. There are many conceivable variations for liberating the supports from the frames in the last step dependent on the specific design of the frames and supports. Some have been described in co-pending application Ser. No. 09/082,038. (See Baum Application at FIGS. 25–28 for various embodiments for removing the supports from the wells and the accompanying discussions pp. 35–40.) Gears 70, like lanterns 10, are made of polypropylene with a thin layer of polystyrene on its surface that has been functionalized to react with reagents used in synthesizing the compound libraries. As shown in FIG. 8 gear 70 comprises a tubular structure with 10 short outwardly projecting fins evenly spaced around the circumference of gear 70. The outer diameter of gear 70 is approximately 4.0 mm to 6.0 mm, preferably around 5.0 mm. Library subunits are synthesized on all surfaces of the gears 70.

Figure 9:
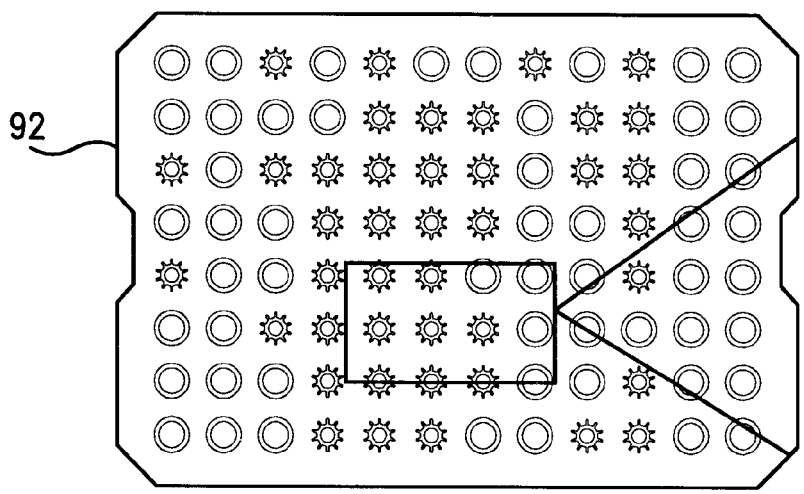
FIG. 9 is a top view of a gear frame that may be used in all embodiments of the present invention.

One type of gear frame suitable for use with gears 70 is shown in FIG. 9. Gear frame 92 is made of high density polyethylene or polypropylene. Gear frame 92 includes 96 apertures arranged in a 8×12 array. The apertures extend through the thickness of gear frame 92 such that rods may be passed through both gears 70 and gear frame 92. Of course, gear frames with greater than or less than 96 apertures may be manufactured. Gears 70 are maintained in the apertures of gear frame 92 by a friction fit or interlocking. Gear frame 92 also may be fitted with one or more radio-frequency identification (RFID) chips to confirm the identification of gear frame 92 and gears 70 within gear frame 92.

Figure 10:
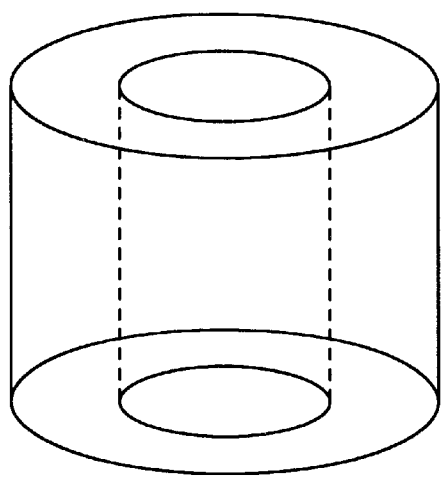
FIG. 10 is a perspective view of a solid-phase support shaped as a ring.

In yet another illustrative example, manipulation of solid-phase supports is minimized through use of a plate that functions both as a container to maintain the solid-phase supports in a 3D array and as a reactor for the various reaction steps. In this example, a combinatorial library having 576 compounds is synthesized on solid-phase supports, which comprise tubes cut into individual solid-phase support rings. As discussed above and shown in FIG. 10, tube rings are structurally similar to lanterns, having a tubular structure with an outer diameter of approximately 7.8 mm, an inner bore diameter of approximately 6.9 mm, and a height of approximately 3.1 mm. Each tube ring supports approximately 15 $\mu$mols of compound, which is approximately 6 mg of compound at an average molecular weight of 400.

Figure 11:
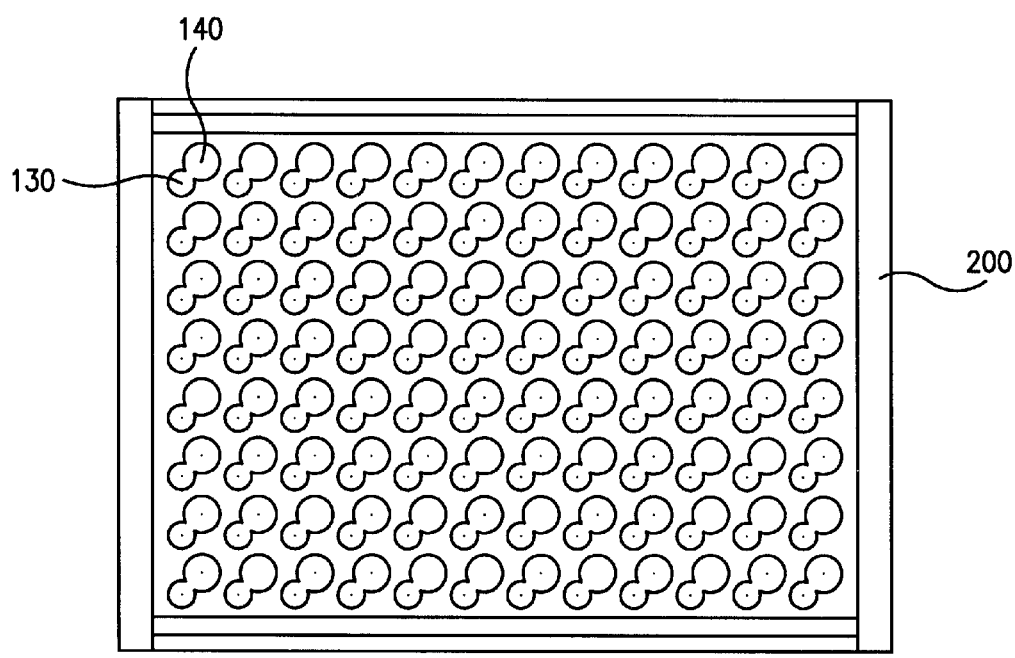
FIG. 11 is a top view of a 3-D containment plate having double-drilled holes for wells.

FIG. 11 illustrates a 96 wells or holes, 3-D containment plate 200 which can be used in the first embodiment of this present invention. Typically such a plate will have 96 holes or more. Note the double-drilled first hole 130 and second hole 140. The two holes intersect and connect the two holes. The first hole is intended to be a channel or well for which the solid supports may be inserted and stacked inside. The second hole is intended to provide a separate channel for reagents to flow through and contact each stacked solid support in the first channel. Since the holes intersect, there is an opening between the first and second channels where the reagent may pass through. Later, when the solid supports need to be retrieved, a rod having a stop-end at one end may be used to pull the stacked column of supports out of the 3-D array by inserting a first end of the rod into the second channel and a bend in second end of the rod is used to catch the end of the column of supports stacked in the first channel. The first end of the rod can be pulled to free the friction fitted or interlocked gears from the frames.

C. "Sort and Combine" Synthesis Using Frames

The third embodiment, in accordance with the present invention, comprises a "sort and combine" synthesis using 2-D frames having N row by M column of solid supports. This method is suitable for large scale production of combinatorial libraries wherein the numbers of unique compounds exceed 100,000. A frame is prepared by placing supports having the same monomer or building block into the first column, filling all N places. The second column of the frame is filled with another set of supports all having the same monomer but different from the monomer in the first column. Each column is thus filled with supports having different monomers attached to the supports.

If Q numbers of identical frames are used, prepared as described above, there should be Q reactors, each having a different reagent. Each frame numbered 1 through Q is immersed in its own reactor to allow the supports on the frames to react with a reagent. After this step, each frame 1 through Q is then taken from the reactors and physically split into subframes of rows of the original frame. Next, all of the subframes are reassembled in groups such that all of the same numbered rows 1 of each original N×M frame are assembled into one group of subframes, all rows 2 of each original frame are assembled into another group of subframes and so on until the last, Nth row of each original N×M frame is assembled into a group of subframes. After reassembly there are N groups of subframes. In the second synthesis step, each of these groups in turn is immersed into N number of different reagents to provide M×N×Q diversity. Q, which represents the number of original frames and also the number of reactors, is independently chosen.

Figure 12:
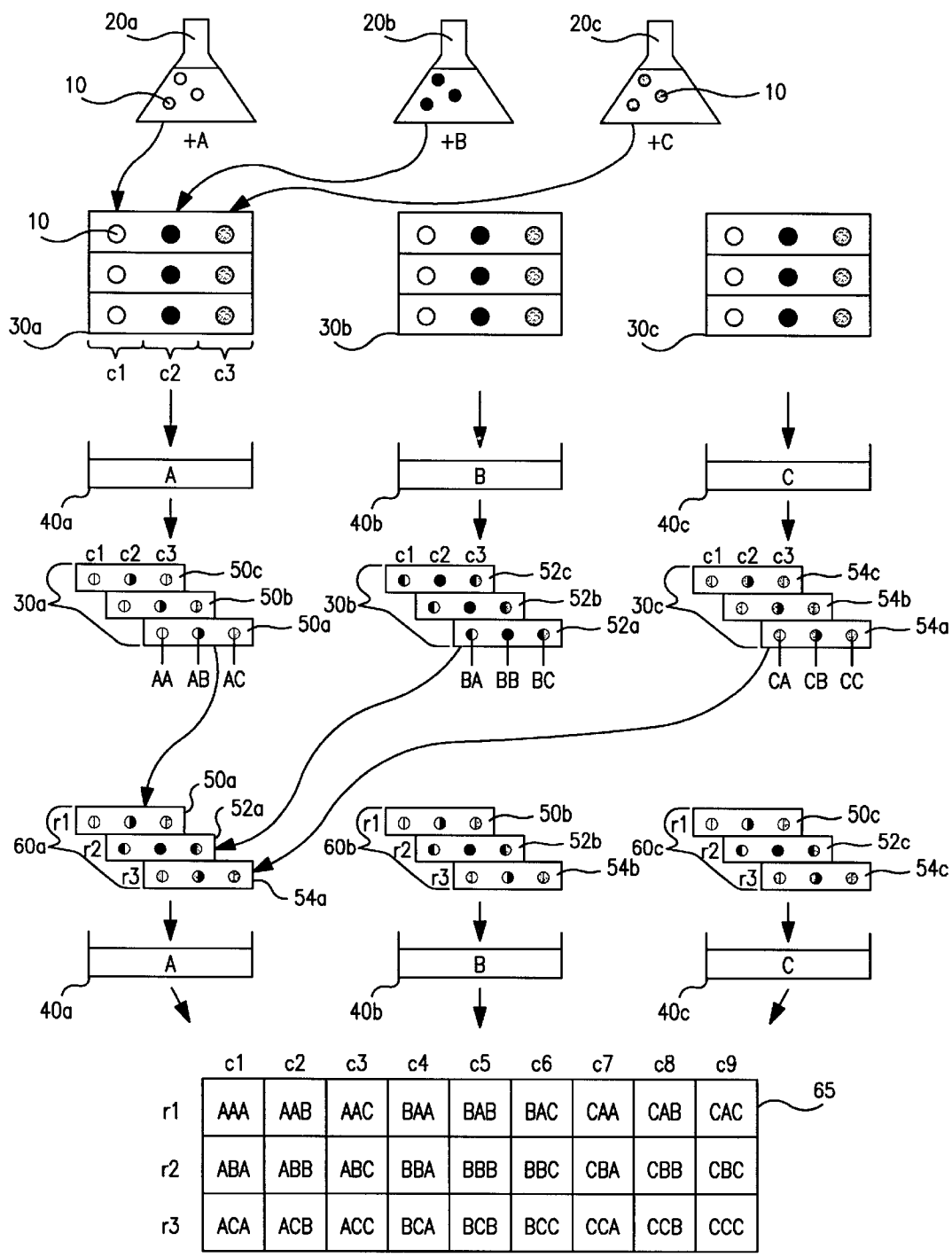
FIG. 12 is a schematic diagram illustrating an embodiment of the present invention used to synthesize a library having 27 subunits.
Figure 13:
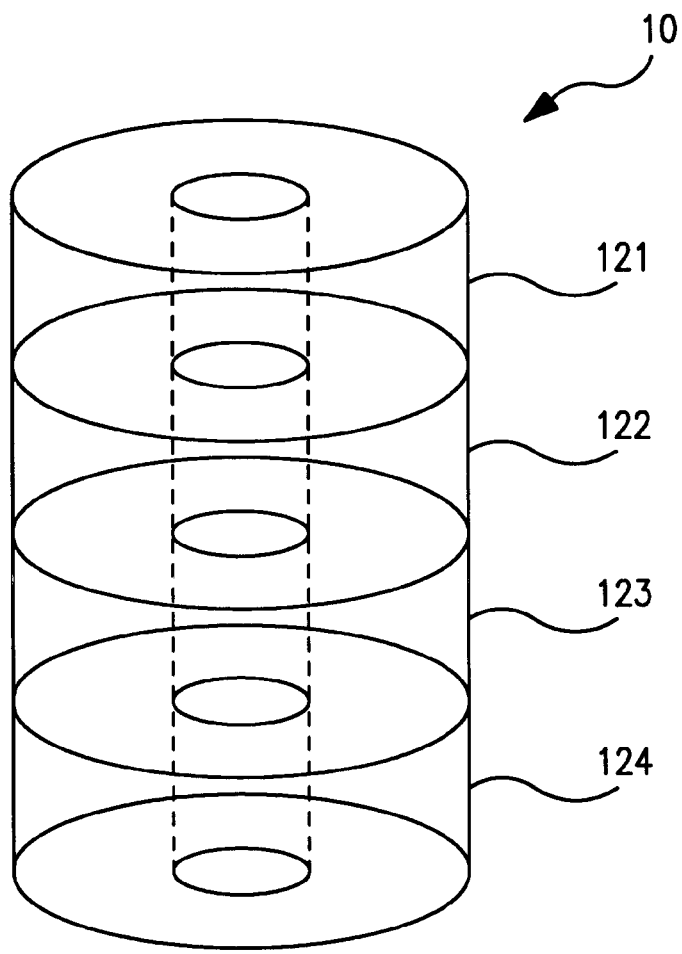
FIG. 13 is a perspective view of a Chiron lantern solid support.

FIG. 12 provides an example of the preferred implementation of the method in accordance with the present invention. While the method may be used to synthesize highly complex libraries, i.e., greater than about 100,000 compounds per library, the following example illustrates synthesis on a much smaller scale in order to provide a simplified, yet complete, explanation of the method.

In this example, a library of only 27 different compounds will be synthesized on solid-phase supports. Each final compounds is composed only of three subunits or building blocks: A, B, and C. The 27 compounds are ultimately arranged in a 2D spatial array, wherein the chemical composition of the compound may be determined by its unique 2D spatial address.

Many known types of free, solid supports may be used with this method. We have already described Chiron lanterns and gears which may be friction-fitted into the holes in frames. We will assume in this example that Chiron lanterns 10, as depicted in FIG. 13, are used.

Referring to FIG. 12, in the first round of synthesis, 27 identical lanterns 10 are reacted with a first reagent A, B, or C, in a manner known in the art, e.g., as described in the Lebl '696 patent. The 27 solid-phase supports 10 are evenly distributed into three reaction flasks 20a, 20b, and 20c. The flasks are essentially reactors except that flasks have smaller volumes. After the first synthesis step is completed, nine lanterns in flask 20a will have attached the A subunit, nine lanterns in flask 20b will have attached the B subunit, and nine lanterns in flasks 20c will have attached the C subunit.

The groups of nine lanterns from each flask are then rearranged into the holes of three lantern frames 30a, 30b, and 30c by friction-fitting the lanterns. It is necessary that each lantern frame be provided equal numbers of lanterns from each flask in an orderly arrangement. In this case each flask A, B and C contributes three lanterns. Note that in this example, each frame 30a, 30b and 30c has the identical 2-D spatial arrangement of lanterns. For each lantern frame 30a–c, lanterns from first flask 20a are placed in the first column (c1), lanterns from second flask 20b are placed in column (c2), and lanterns from third flask 20c are placed in the column (c3) farthest to the right. Note that this is but one example of a workable orderly arrangement. Other arrangements can serve equally well as long as each frame is provided lanterns in equal numbers from each different flask available, and the arrangement is orderly and known.

In the second synthesis step, each frame 30a, 30b, and 30c is then reacted with a second set of reagents, also having subunits A, B, and C, by immersing each frame into its respective reactors, 40a, 40b and 40c. Note that subunits may be the same subunits in the first synthesis step as the example provided. However, within a synthesis step, each subunit provided in each reactor should be unique.

As a result of the second round of synthesis, the lantern frames 30a, 30b, 30c contain nine different two-subunit synthesis intermediates. The lanterns in frame 30a will have three different synthesis intermediates as follows: in column c1, three lanterns having the intermediates AA; in column c2, three lanterns having the intermediates AB; and in column c3, three lanterns having the intermediates AC. The lanterns in frame 30b will have three different synthesis intermediates as follows: in column c1, three lanterns having the intermediates BA; in column c2, three lanterns having the intermediates BB; and in column c3, three lanterns having the intermediates BC. Similarly, the lanterns in frame 30c will have three different synthesis intermediates as follows: in column c1, three lanterns having the intermediates CA; in column c2, three lanterns having the intermediates CB; and in column c3, three lanterns having the intermediates CC.

The next step provides a randomization. Each row of the frame 30a is then broken into smaller subframes of rows as indicated by subframes 50a, 50b, and 50c. Each split subframe has three supports. Frame 30b is broken into smaller subframes 52a, 52b and 52c. And similarly, frame 30c is broken into subframes 54a, 54b and 54c. The subframes are regrouped such that all split frames from the same rows are grouped together. For example, subframes from the first rows, 50a, 52a and 54a are grouped into new group of subframes 60a. Subframes from the second rows, 50b, 52b and 54b are grouped into a new group of subframes 60b. Similarly, subframes from the third rows, 50c, 52c, and 54c are grouped into new group of subframes 60c.

In the third synthesis step, each new group of subframes, 60a, 60b and 60c, is immersed into reactors 40a, 40b, and 40c, respectively. Note that in this example, the same reactors that were used in the second round of synthesis are used again in this third round of synthesis. Alternatively, other reactors (not shown) having different subunits, e.g., H, I, and J may be used. After the third round of synthesis, all 27 of the possible three unit combinations of building blocks A, B, and C will have been synthesized. Each compound will be attached to and located on one and only one lantern.

In an alternative embodiment, smaller frames may be used in lieu of a breakable larger frame. Specifically, in this example, rather than using the three lantern frames 30a–c, which are adapted to contain 9 lanterns apiece, one can use nine smaller frames, which are adapted to contain 3 lanterns apiece.

All 27 lanterns 10 are then removed from their respective subframes, and transferred to plate 65 comprising a 3 row by 9 column (3×9) array of wells. The compounds are then removed from the lanterns, such that there is one unique compound per well. Therefore, each compound has a unique location or spatial 2D address within the plate, i.e., row (1–3), column (1–9), and may therefore be identified by its unique spatial 2D address. For example, compounds located in well at r2, c5 will have a chemical composition comprising BBB. According to the spatial 2D address, one can therefore determine the chemical composition of the compound.

As explained above, each lantern 10 moves through a given pattern throughout synthesis such that its ultimate location or spatial address reveals the chemical composition of the compound attached to each lantern. In addition, the spatial address of each compound and its associated chemical composition will also reveal the history of the synthesis, including the various rounds or reactions of synthesis. For example, by its spatial address within the 3×9 plate, it may be determined which flask the compound originated from in the first round of synthesis. The spatial address therefore contains a wealth of useful information about the compound.

In addition, the present method is not limited to any particular pattern or grouping of solid-phase supports. Any ordered, nonrandom pattern or grouping may be incorporated into the present method as long as the relationship between the pattern and the ultimate spatial address of the library compounds is determinable. For example, in an alternative embodiment of the present method, the lanterns may first be arranged such that the 9 lanterns from the first flask comprise the first row (rather than column) of each 3×3 lantern frame.

Lantern 10 is known in the art and is commercially available from Chiron. Lantern 10 is made of polypropylene with a thin layer of polystyrene on its surface similar to other solid-phase supports known in the art. This polystyrene surface is functionalized to react with reagents used in synthesizing the compound libraries. As shown in FIG. 13, a lantern comprises four tubular substructures, 121, 122, 123, and 124, that are attached to each other, creating an overall tubular structure. Lantern 10 has an outer diameter of approximately 5.0 mm to approximately 6.0 mm, preferably around 5.0 mm, and an inner bore with a diameter of approximately 2.0 mm to approximately 3.0 mm, preferably around 2.5 mm. In addition, the height of each lantern is approximately 5 mm. In addition, each lantern 10 supports approximately 15 $\mu$mols of compound. Library subunits are synthesized on all surfaces of the lanterns, including both the outer and inner surface. Although lanterns are used in the preferred embodiment of the present method, it will be appreciated by those of ordinary skill in the art that any physically manipulable solid-phase support may be incorporated into the present method. Tubes cut into individual solid-phase support rings may also be used.

Figure 14A:
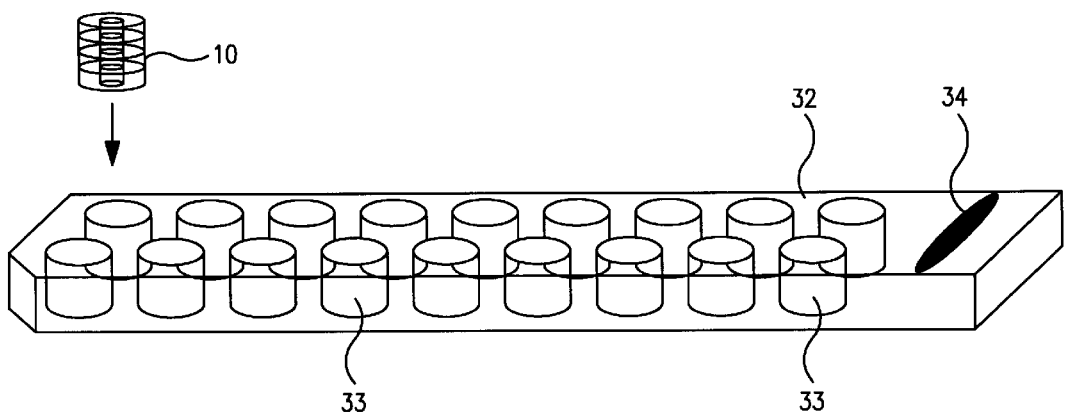
FIG. 14a is a perspective view of a frame used to contain solid-phase supports, the frame having an RFID chip.
Figure 14B:
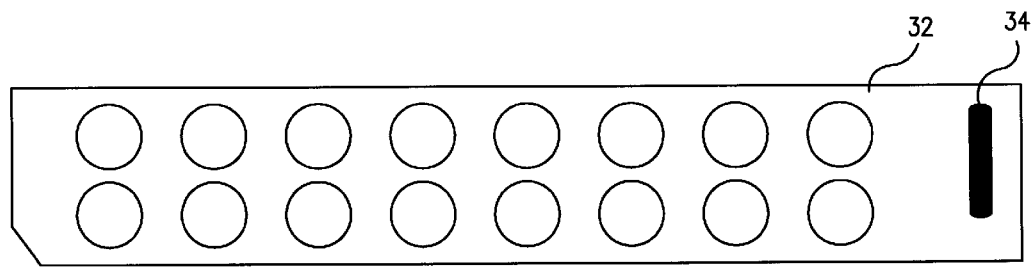

A preferred type of lantern frame that may be used in the present method is shown in FIGS. 14a and 14b. Frame 32 comprises a high density polyethylene, polypropylene, or other chemically resistant material and has dimensions of approximately 18 mm by 81 mm. Frame 32 includes 16 wells 33 arranged in a 2×8 array, and wells 33 are dimensioned to contain lanterns 10. In addition, frame 32 includes knife cut grooves (not shown) that allow it to be divided or broken apart into subframes having at least two wells apiece. Optionally, frame 32 may be fitted with one or more radio-frequency identification (RFID) chips 34 known in the art to record the identity of frame 32 and lanterns 10 within frame 32. RFID chip 34 is approximately 11 mm long and is positioned at one end of frame 32. In addition, a variety of alternative structural supports may be incorporated into the present invention.

In sum, the apparatus comprises: (a) single frames which can be broken into subframes; (b) reactors; and (c) means for holding solid supports on the frames temporarily or means to allow cutting of the supports.

The present invention may be embodied in other forms without departing from its spirit or essential characteristics. The described embodiments are to be considered only as illustrative and not as restrictive. For example, in each of the examples described above, each synthesis comprises three rounds of reactions. However, depending on the combinatorial library desired, one may need fewer than three rounds or less than three rounds. The scope of the invention is, therefore, indicated by the appended claims.

What is claimed:

1. A method of synthesizing combinatorial libraries comprising:

providing Q numbers of 2-D frames, each an array of N rows by M columns of holes with supports inserted therein, wherein the supports in each hole of a column have attached the same building block diverse from the building blocks attached to the supports in the holes of the other columns;

immersing said 1 to Q 2-D frames into respective 1 to Q reactors, each having different reagents, thereby allowing each support building block to react with a respective reagent;

separating each 2-D frame into N subframes, each consisting of an individual 1 by M row of said 2-D frame;

regrouping one subframe from the same row of each original 2-D frame to form N numbers of 2-D frames, each an array of Q rows by M columns of holes with supports inserted therein; and immersing the 1 to N 2-D frames into a respective set of 1 to N reactors, each containing a different reagent.

2. The method of claim 1 wherein said 2-D frames are breakable into individual rows, and said separating step comprises physically breaking said breakable 2-D frame into said N subframes consisting of individual 1 by M rows.

3. The method of claim 1, further comprising:

transferring the solid supports from a 1 to N 2-D frame to a plate comprising a corresponding 2-D Q by M array of wells in rows and columns, so that the spatial addresses of the supports are retained.

4. The method as in claim 1, wherein the solid supports are lanterns.

5. The method as in claim 4, wherein the lanterns are made of polypropylene with a surface of polystyrene and having a tubular structure with an outer diameter of from about 4.0 mm to about 6.0 mm and an inner bore diameter of from about 2.0 mm to about 3.0 mm.

6. The method of claim 5, wherein the outer diameter of each lantern is about 5.0 mm, and the inner bore diameter is about 2.5 mm.

7. The method as in claim 1, wherein the solid supports are gears, having a tubular structure with a plurality of outwardly projecting fins.

8. The method of claim 7, wherein the gear is made of polypropylene with a surface of polystyrene and having an outer diameter of from about 4.0 mm to about 6.0 mm.

9. The method of claim 8, wherein the outer diameter of each gear is about 5.0 mm.

10. The method as in claim 1, wherein the solid supports are rings, having an inner borehole and an outer diameter.

11. The method of claim 10, wherein the rings are made of polypropylene with a surface of polystyrene, with an outer diameter of from about 7.8 mm, an inner bore diameter of about 6.9 mm, and a height of about 3.1 mm.

12. The method of claim 1, further comprising a radio frequency identification (RFID) chip attached to a frame or subframe.

* * * * *